United States Patent
Asano

(10) Patent No.: US 9,847,006 B2
(45) Date of Patent: Dec. 19, 2017

(54) FALL DETECTOR AND ALERT SYSTEM

(71) Applicant: Shintaro Asano, New Castle, NH (US)

(72) Inventor: Shintaro Asano, New Castle, NH (US)

(*) Notice: Subject to any disclaimer, the term of this patent is extended or adjusted under 35 U.S.C. 154(b) by 0 days.

(21) Appl. No.: 15/063,037

(22) Filed: Mar. 7, 2016

(65) Prior Publication Data

US 2016/0260311 A1 Sep. 8, 2016

Related U.S. Application Data

(60) Provisional application No. 62/128,582, filed on Mar. 5, 2015.

(51) Int. Cl.
| | |
|---|---|
| G08B 23/00 | (2006.01) |
| G08B 21/04 | (2006.01) |
| A43B 3/00 | (2006.01) |
| G08B 25/01 | (2006.01) |
| G08B 25/08 | (2006.01) |
| A43B 17/00 | (2006.01) |
| A62B 33/00 | (2006.01) |
| A61B 5/11 | (2006.01) |

(52) U.S. Cl.
CPC ........ *G08B 21/0446* (2013.01); *A43B 3/0005* (2013.01); *A43B 3/0015* (2013.01); *A43B 17/00* (2013.01); *A61B 5/112* (2013.01); *A61B 5/1117* (2013.01); *A62B 33/00* (2013.01); *G08B 25/014* (2013.01); *G08B 25/08* (2013.01)

(58) Field of Classification Search
CPC .. G08B 21/0446; G08B 25/014; G08B 25/08; A43B 3/0015
USPC .......................................... 340/573.1, 539.11
See application file for complete search history.

(56) References Cited

U.S. PATENT DOCUMENTS

| | | | | |
|---|---|---|---|---|
| 6,967,044 | B1* | 11/2005 | O'Brien | A43B 13/10 36/153 |
| 2003/0093921 | A1* | 5/2003 | Elul | A43B 13/18 36/28 |
| 2003/0200679 | A1* | 10/2003 | Wilson | A43B 7/125 36/55 |

(Continued)

FOREIGN PATENT DOCUMENTS

WO 00/78170 A1 12/2000

OTHER PUBLICATIONS

Int'l Search Report and Written Opinion, dated May 27, 2016, PCT/US16/21220, 13 pages.

*Primary Examiner* — Ojiako Nwugo
(74) *Attorney, Agent, or Firm* — The Juhasz Law Firm, P.C.

(57) ABSTRACT

A fall detection and alert system and associated methods are described. The system includes a right footwear item and a left footwear item, each of which includes foot pressure sensors, communications circuitry configured to transmit foot pressure signals from the pressure sensors to a mobile device, such as a smartphone, and a power source. The system also includes an application for the mobile device that causes the mobile device to receive transmitted foot pressure signals from the communications circuitry of the footwear, analyze the foot pressure signals to determine whether a wearer of the footwear items has fallen, display a warning if it is determined that the wearer of the footwear items has fallen, along with an option to cancel the warning, and send a signal to a caregiver if the warning has not been canceled within a predetermined period of time.

15 Claims, 7 Drawing Sheets

(56) References Cited

U.S. PATENT DOCUMENTS

| | | | |
|---|---|---|---|
| 2007/0006489 A1* | 1/2007 | Case | A43B 3/0005 36/132 |
| 2009/0128320 A1 | 5/2009 | Needham et al. | |
| 2009/0135001 A1* | 5/2009 | Yuk | A43B 5/00 340/539.11 |
| 2009/0137933 A1 | 5/2009 | Lieberman et al. | |
| 2013/0000156 A1* | 1/2013 | Andoh | A43B 3/0005 36/136 |
| 2013/0130843 A1* | 5/2013 | Burroughs | A63B 71/0686 473/415 |
| 2013/0274587 A1 | 10/2013 | Coza et al. | |
| 2014/0222173 A1* | 8/2014 | Giedwoyn | A43B 3/0005 700/91 |
| 2015/0260514 A1* | 9/2015 | Menelas | A43B 3/0005 702/2 |
| 2016/0174899 A1* | 6/2016 | Besnard | A43B 3/0005 600/595 |

* cited by examiner

FALL DETECTOR AND ALERT SYSTEM

CROSS-REFERENCE TO RELATED APPLICATIONS

The present application claims the benefit of U.S. Provisional Application 62/128,582, filed Mar. 5, 2015, and entitled "Fall Detector", the entirety of which is incorporated herein by reference.

FIELD

Embodiments of the disclosure relate generally to a system for detecting falls, and for alerting a caregiver that a person has fallen. More specifically, the disclosure relates to using pressure sensors placed in an insole or other footwear to detect a fall, and to communicating wirelessly with a caregiver if a fall has occurred.

BACKGROUND

The populations of developed countries worldwide are ageing quickly. For example, in the United States of America, demographic statistics indicate that there are currently (as of 2016) around 49 million people who are 65 years of age or older, accounting for about 15% of the total population. The population that is 65 or older is projected to grow at a rate of about 1.8 million per year in the US, so within ten years, the number is expected to be around 67 million—about 19% of the total projected population. The percentage of the population that will be 65 or older is expected to increase even more rapidly in many other developed countries, including many European countries, and Japan.

As the elder population increases, the need for protecting them from falling is becoming increasingly important. According to medical statistics, about one million elderly people fall each month, and roughly 45% of them either pass out or are otherwise incapable of reporting their fall immediately, to call for assistance.

SUMMARY

Based on the above, there is a growing need for fall detection. Conventional fall detectors often employ tri-axis accelerometers and gyroscopes to detect falls. Typically, these sensors are mounted inside a small container worn by the user on a lanyard around his/her neck, or attached to the belt. These methods provide only an indirect measurement, and are often apt to produce both "false positive" and "false negative" results. A false positive means that the device reports that a fall occurred when the user did not fall, while, more worryingly, a false negative means that the device fails to report a fall when the user has actually fallen. Either way, this type of error in reporting significantly reduces trust in the system by users, and often results in disuse of such systems.

Embodiments of the present disclosure apply a different, more direct approach to detecting falls. Since "falling down" means that the pressure or weight of the person on the bottom of his or her foot (which contacts the insole of a shoe, or other footwear) has dropped to zero or nearly zero. Accordingly, pressure sensors located in an insole or in other footwear are used to determine when a user has fallen, by detecting a drop in the pressure on the bottom of the user's foot to zero or nearly zero.

In one general aspect, a fall detection system includes a right footwear item and a left footwear item. Each of the right and left footwear items includes at least two foot pressure sensors, communications circuitry configured to transmit foot pressure signals from the at least two pressure sensors to a mobile device, and a power configured to provide power to the communications circuitry. The system also includes a mobile device executing an application that causes the mobile device to receive transmitted foot pressure signals from the communications circuitry of the footwear, analyze the foot pressure signals to determine whether a wearer of the footwear items has fallen, display a warning if it is determined that the wearer of the footwear items has fallen, along with an option to cancel the warning, and send a signal to a caregiver if the warning has not been canceled within a predetermined period of time.

In some embodiments, the application causes the mobile device to analyze the foot pressure signals by determining that the wearer of the footwear items has fallen if the foot pressure signals from both the right footwear item and the left footwear item indicate a drop to zero or nearly zero pressure. In some embodiments, the application further causes the mobile device to determine and store a normal foot pressure pattern for the wearer of the footwear items, based on the foot pressure signals received from the footwear items. In some of these embodiments, the application further causes the mobile device to display a warning if there is a sudden deviation from the normal foot pressure pattern for the wearer of the footwear items, along with an option to cancel the warning.

In some embodiments, the at least two foot pressure sensors include a front foot pressure sensor, configured to be located approximately beneath a ball of a wearer's foot, and a rear foot pressure sensor, configured to be located approximately beneath a heel of the wearer's foot. In some embodiments, the right footwear item and the left footwear item may be insoles. In some embodiments, the footwear items may be a shoe, a sock, a slipper, or a boot. In some embodiments, at least one of the right footwear item and the left footwear item is built into or attached to a prosthetic device or walking assistance device. In some embodiments, the at least two pressure sensors, the communication circuitry, and the power source are contained within a flexible enclosure that is impervious to liquids.

In some embodiments, the power source includes a rechargeable power source. In some embodiments, each of the right footwear item and the left footwear item further includes an induction charger for recharging the rechargeable power source. In some embodiments, each of the right footwear item and the left footwear item further includes a plurality of piezo elements that generate power for recharging the rechargeable power source. In some embodiments, the at least two foot pressure sensors include piezo elements that sense foot pressure and that generate power for recharging the rechargeable power source.

In some embodiments, each of the right footwear item and the left footwear item includes a kinetic generator that generates power for recharging the rechargeable power source. The kinetic generator may include a swing pendulum having a magnetic portion, and a coil. The swing pendulum may be configured such that when the wearer of the footwear is walking, the magnetic portion of the swing pendulum sweeps across the coil to generate power. The kinetic generator may further include two stops disposed so that the swing pendulum strikes one of the stops at each end of its swinging motion, and at least one of the stops may include a piezo element that generates power for recharging the rechargeable power source.

In some embodiments, each of the right footwear item and the left footwear item further includes a controller. In some embodiments, the communications circuitry includes circuitry for communicating over a wireless body area network or a wireless personal area network. In some embodiments, the communications circuitry includes Bluetooth circuitry. In some embodiments, the mobile device is a smartphone.

In another general aspect, a method of detecting a fall includes receiving transmitted foot pressure signals from at least two pressure sensors disposed in each of a right footwear item and a left footwear item, determining that the wearer of the footwear items has fallen if the foot pressure signals from both the right footwear item and the left footwear item indicate a drop to zero or nearly zero pressure, displaying a warning if it is determined that the wearer of the footwear items has fallen, along with an option to cancel the warning, and sending a signal to a caregiver if the warning has not been canceled within a predetermined period of time. In some embodiments, the method further includes storing a normal foot pressure pattern for the wearer of the footwear items, based on the foot pressure signals received from the footwear items, and displaying a warning if there is a sudden deviation from the normal foot pressure pattern for the wearer of the footwear items, along with an option to cancel the warning. Other embodiments of this aspect may include corresponding computer systems, apparatus, and computer programs recorded on one or more computer storage devices, each configured to perform the actions of the methods.

In another general aspect, a fall-detection footwear item includes at least two foot pressure sensors, communications circuitry configured to transmit foot pressure signals from the at least two pressure sensors to a mobile device, and a rechargeable power source connected to the communications circuitry, the power source providing power to the communications circuitry. The at least two pressure sensors, the communication circuitry, and the rechargeable power source are contained within a flexible enclosure that is impervious to liquids.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the disclosure. In the following description, various embodiments of the disclosure are described with reference to the following drawings, in which.

DESCRIPTION

As noted above, conventional fall detection systems typically use accelerometers and gyroscopes to detect falls. These methods provide an indirect measurement, and may be prone to both false positive and false negative results. Additionally, fall detection systems that are used outside of a small, confined area often include costly and complex wide-area communication systems, so that a caregiver can be alerted when a fall occurs.

Embodiments of the present disclosure apply a more direct approach to detecting falls, by using pressure sensors in an insole or other footwear, such as shoes, slippers, or socks, to detect a fall. A fall may have occurred if the pressure sensors detect a drop in the pressure from the foot on the sensors to zero or nearly zero.

Because the sensors in accordance with various embodiments of the present disclosure may be built into insoles or other footwear, it may be desirable for the sensors and other electronics to be relatively robust, and sealed in such a way that the system is substantially waterproof, to handle both sweat and washing. Because most footwear must be replaced relatively frequently, it may be desirable, in some embodiments, for the replaceable portions to be relatively low-cost, while keeping high-cost components, such as cellular or wide-area communications, and a display for interacting with the user separate from the insole or other footwear. Finally, because an insole or other footwear may have little space for electronic components, the power-source that is employed may have a limited capacity. Accordingly, it may be desirable, in some embodiments, to have a rechargeable or easily replaceable power source.

Figure 1:
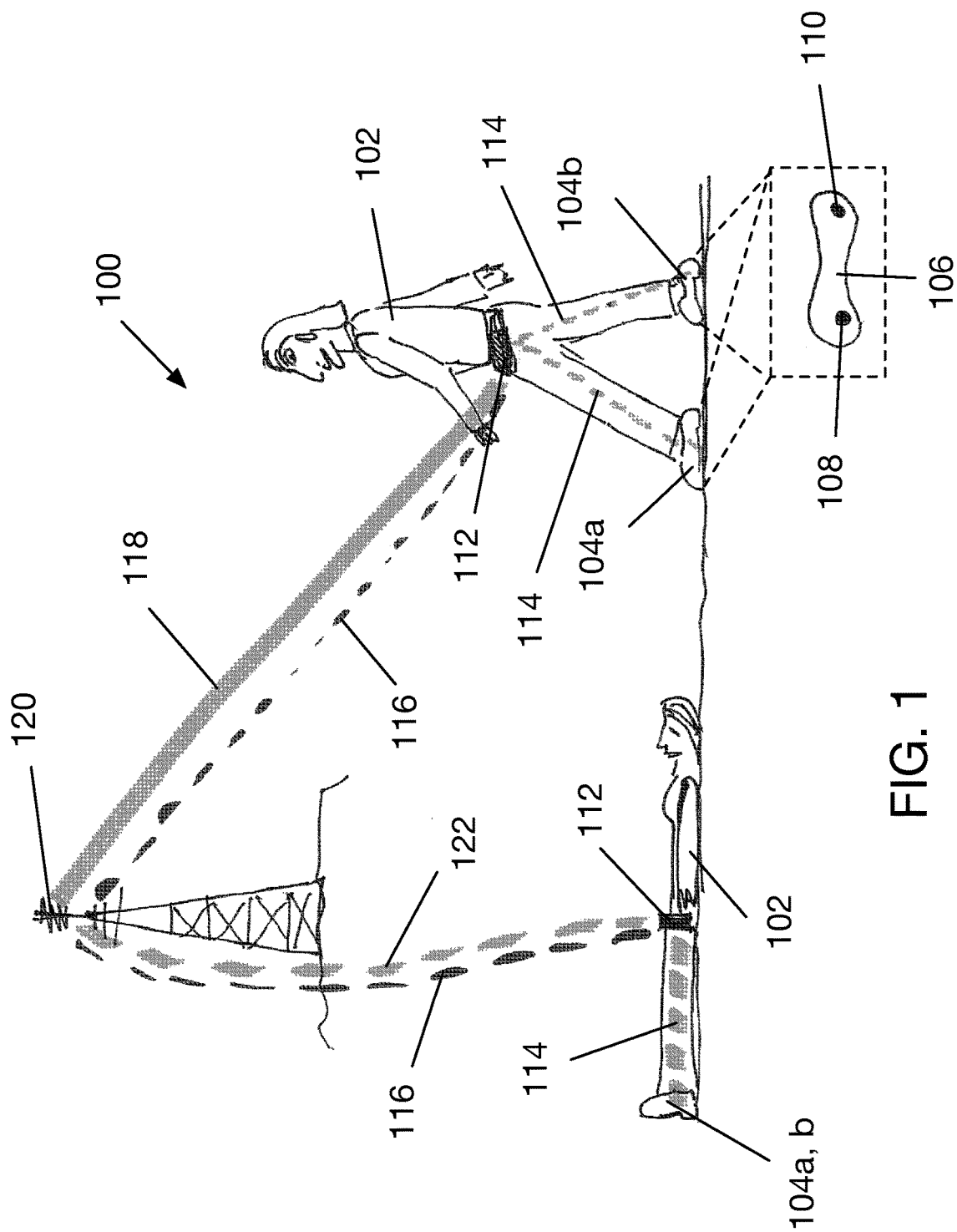
FIG. 1 shows an overview of a fall detection system in accordance with an embodiment of the disclosure.

FIG. 1 shows an overview of a system 100 in accordance with various embodiments of the disclosure. The system may include footwear items 104a and 104b, which may be shoes, socks, slippers, boots, or the like. In some embodiments, the footwear items 104a and 104b may be insoles or insole inserts, which are placed into shoes or other footwear that that is worn by a user 102. The footwear items 104a and 104b generally include a right footwear item 104a and a left footwear item 104b (collectively, "footwear items" or "footwear"), worn by the user 102 on his or her right and left feet, respectively. Some users may have only one foot (or in some cases, none), in which case, it will be understood that at least one of the right footwear item 104a and/or the left footwear item 104b may be integrated into or worn on a prosthetic, such as a prosthetic foot or leg, or integrated into or attached to a cane, a crutch, or other assistance device.

Each footwear item 104a and 104b may include a base 106, such as a sole or insole that is beneath the foot of the user 102. Each base 106 includes two pressure sensors. A front pressure sensor 108 may be located under the ball of the foot, and a rear pressure sensor 110 may be located under the heel. The pressure sensors 108 and 110 may be any kind of pressure or force sensor, such as force-sensitive resistors or piezoelectric force sensors.

It should also be noted that while, in some embodiments, pressure may be detected at least under a front portion of the foot, such as the ball of the foot, and under a rear portion of the foot, such as the heel, other sensor placements are possible. Additionally, various embodiments could also function with more than two sensors, or using sensors that, for example, detect pressure under substantially the entire foot.

The bases 106 may communicate via near-field communications (NFC), a wireless body area network (BAN), a wireless personal area network (PAN), or via other relatively short-range and low-power wireless communications channels 114 (though wired communication is also possible) with a mobile device 112, such as a mobile phone or other mobile device that can be carried by the user 102. In some embodiments, the bases 106 may include Bluetooth communication circuitry (not shown), so that the communication channels 114 transfer data using Bluetooth. In some embodiments, the bases 106 may include NFC communication circuitry (not shown), so the communication channels 114 transfer data using NFC. In some embodiments, the bases 106 may include BAN circuitry, such as a transceiver capable of use with the IEEE 802.15.6 standard, so the communication channels 114 transfer data via a BAN. In addition to communication circuitry, each of the bases 106 may also include a controller or other processing circuitry (not shown), which may handle, among other tasks, handling a communications protocol that may be used for establishing the communication channels 114, and for transferring data between the mobile device 112 and the bases 106 via the communication channels 114. Each of the bases 106 may also include a battery or other power sources (not shown), which, as will be described in greater detail below, may include a rechargeable power source.

In some embodiments, the mobile device 112 may be a cellular telephone, for example, a smartphone, such as an IPHONE smartphone, manufactured by Apple Inc., of Cupertino, Calif., or a smartphone operating under the ANDROID mobile operating system, developed by Google Inc., of Mountain View, Calif., a smartphone operating under a WINDOWS mobile operating system, developed by Microsoft Corporation, or Redmond, Wash., or any other smartphone. Such smartphones typically are mobile phones that have significant processing capabilities, and that operate under a mobile operating system, that is capable of executing third-party applications, or "apps". Smartphones typically include a processor, memory, communication circuitry, and a display, typically a touchscreen display, through which the smartphone can interact with a user. Most smartphones can access the Internet wirelessly, can communicate wirelessly using Bluetooth communication technologies, and can access wireless local area networks, in addition to their cellular or and other wide-area communications capabilities. Many smartphones also include Global Positioning System (GPS) circuitry, and are capable of using GPS to determine the location of the smartphone. Smartphones may also include a variety of other circuitry, such as digital cameras, audio circuitry, fingerprint scanners, and other input or output devices and their associated circuitry.

In some embodiments, because the mobile device 112 handles functions such as wide-area communications or communications over a wireless local area network, location determination, significant processing functions, and interacting with the user 102, the relatively costly and complex hardware that carries out these functions need not be present in the footwear. This may make the footwear less costly, so that it is not too costly to replace when it becomes worn, has been washed too many times, or should otherwise be replaced.

In use while the user 102 is walking, as shown in the right-hand portion of FIG. 1, the mobile device 112 may receive information from the sensors 108 and 110 in the base 106 of each of the footwear items 104*a* and 104*b*, via the communication channels 114. The mobile device 112 may communicate data 118 via a wide-area communication channel 116, such as a channel over a cellular network 120 or other wide-area communications network. In some embodiments, the mobile device 112 may communicate data 118 over a wireless local area network, in addition to or instead of communication over a wide-area network.

The data 118 may include status updates, location information, or other information. An app running on the processor in the mobile device 112 can use data from the footwear items 104*a* and 104*b* to determine information on walking tempo, gait, weight and weight distribution, and other information that may assist in caring for the user 102, and which may be included in the data 118. In some embodiments, the app may use information provided by the footwear items 104*a* and 104*b* to interpret the time interval regularity and irregularity between the front sensor 108 and rear sensor 110 on both the left and right feet. The app can use this data analysis to determine abnormalities or other conditions, other than just detecting falls. Information on such abnormalities or the results of other data analysis performed on the mobile device 112 may be included in the data 118.

The data 118 may be communicated to a caregiver, such as a medical provider, a designated family member or relative, a friend or network of friends, emergency services, or another service or person who provides care for or is responsible for monitoring the user 102. The caregiver receiving the data 118 may be a predetermined caregiver, and may be someone different than the caregiver who received fall detection signals 122 (see below). In some embodiments the data 118 may be sent to multiple caregivers, or portions of the data 118 can be sent to multiple and/or different caregivers. In some embodiments, communication of data 118 may be optional, while in other embodiments, only fall detection signals 122 will be sent with respect to data collected from the footwear items 104*a* and 104*b*, so there may be no data 118 communicated by the system 100.

In some embodiments, if the user 102 falls, as is shown in the left-hand portion of FIG. 1, the mobile device 112 may receive signals from the footwear items 104*a* and 104*b* over communication channels 114 indicating zero or nearly zero pressure on the bases 106. Alternatively, in some embodiments, the mobile device 112 may stop receiving signals over channels 114 indicating that there is pressure on the bases 106 when the user 102 falls. The mobile device 112 may analyze this information, optionally in combination with other information that has been gathered on the user and/or personal information on the user, to detect a fall. Once the mobile device 112 detects a fall, it may give the user 102 a warning and a warning period, generally between about 10 seconds and about two minutes, to cancel the sending of a fall detection signal. After the warning period, if the user 102 has not cancelled the sending of a fall detection signal, the mobile device 112 may send a fall detection signal 122 to a caregiver (not shown) via the wide-area communication channel 116 and/or a wireless local area network (not shown).

In some embodiments, GPS capabilities of the mobile device 112 will be used to send location information on the user 102, as well as the fall detection signal 122. In some embodiments, the location information will be sent only if it is determined that the user 102 is away from home. In some embodiments, other technologies, such as cell-based location systems, or location systems based on proximity to Wi-Fi or other wireless transceivers may be used to locate the mobile device 112 if GPS is not available. Such systems could also be used to enhance the location information when GPS is available on the mobile device 112.

As discussed above, the caregiver may be emergency services, a medical provider, a designated family member or relative, a friend or network of friends, or another service or person who provides care for or is responsible for monitoring the user 102. The caregiver receiving the fall detection signal 122 may be a predetermined caregiver, and may be someone different than the caregiver who received the data 118. In some embodiments, the fall detection signal may be sent to multiple caregivers.

There may be instances in which zero or near-zero pressure on the bases 106 does not indicate a fall. For example, the user 102 may be seated in a position in which both of his or her feet are out of contact with the floor. In such instances, a false positive (i.e., sending a fall detection signal when there has not actually been a fall) can be avoided by the user responding to a warning on the mobile device 112 by cancelling sending of a fall detection signal during the warning period. In some embodiments, once the sending of a fall detection signal is canceled, no further fall detection signal will be sent until after a pressure on the bases 106 has again been detected for at least a predetermined period of time.

Because the fall detection system 100 monitors the foot pressure of the user 102, rather than relying on less direct measurements, the occurrence of false negatives in fall detection, as well as the occurrence of false positives, may be reduced. Fall detection determinations may be made on the basis of foot pressure data, either transmitted or stored directly or as patterns, without the inclusion of indirect data, such as data from accelerometers or gyroscopes.

Figure 2A:
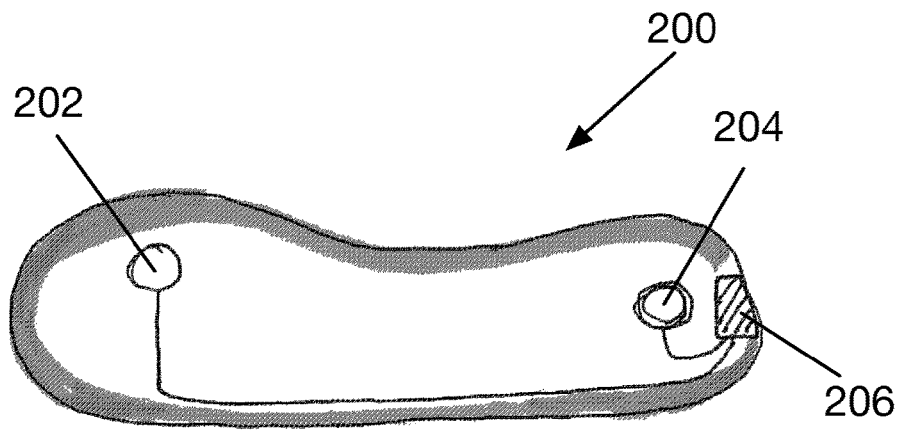
FIGS. 2A and 2B show a top and side view, respectively, of fall-detection footwear in accordance with an embodiment of the disclosure.
Figure 2B:
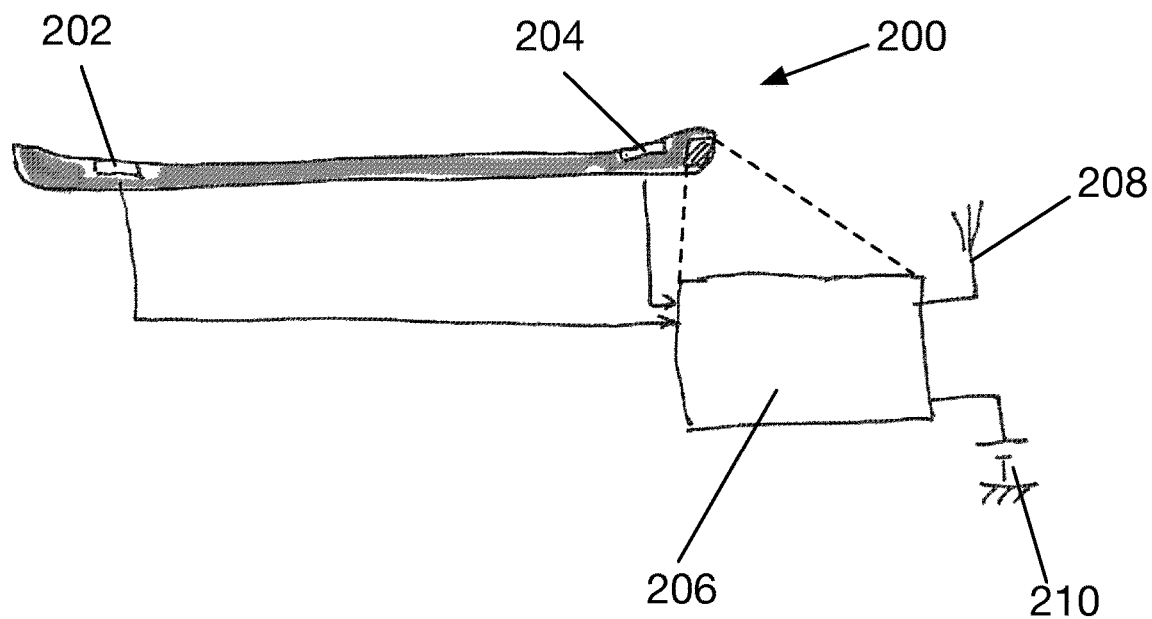

Referring now to FIGS. 2A and 2B, components of an embodiment are described. Although the embodiment is described in terms of an insole, it will be understood that the same configuration could be used, mutatis mutandis, in any other footwear, such as shoes, socks, slippers, boots, and the like, or in prosthetic devices, such as prosthetic feet or legs, or in or attached to a cane, crutch, or other assistance device.

Footwear 200, which is shown for illustrative purposes as an insole, and which may be configured for use with either the left or the right foot, and may be configured for various foot sizes, includes a front pressure sensor 202 and a rear pressure sensor 204. As discussed above, the front pressure sensor 202 and rear pressure sensor 204 may be positioned so that they will be beneath the ball of the foot and the heel, respectively, though other positioning is also possible, as are additional pressure sensors, or sensors that detect pressure under substantially the entire foot. As above, the pressure sensors 202 and 204 may be any kind of pressure or force sensor, such as force-sensitive resistors or piezoelectric force sensors.

The front pressure sensor 202 and the rear pressure sensor 204 are electrically connected to communications circuitry 206. The communications circuitry 206 may be a part of a controller, which may be a microcontroller, such as an nRF51822 microcontroller, manufactured by Nordic Semiconductor ASA, of Oslo, Norway, which integrates Bluetooth communications circuitry with a microcontroller. Alternatively, the controller (not shown separately) may also be separate from the communications circuitry 206. The communications circuitry 206 may be short-range communication circuitry, and may be electrically connected to an antenna 208, which may be integrated into the footwear 200. Additionally, the communications circuitry 206 and controller (whether separate or integrated with the communications circuitry 206) are electrically connected to a battery 210. The controller (not shown separately) may control the gathering of data from the pressure sensors 202 and 204, control the transmission of data via the communication circuitry 206, and may perform other control functions in the footwear 200.

In the illustrative embodiment shown in FIGS. 2A and 2B, the circuitry, including the communications circuitry 206 and the battery 210, are shown as being embedded in a rear portion of the footwear 200. This positioning may provide access to the battery 210, if the battery 210 needs to be changed or removed. Other positions for the communications circuitry 206 and battery 210 within the footwear 200 are also possible, including, but not limited to, a position in a center portion of the footwear 200. Additionally, the communications circuitry 206 may be in a different location within the footwear 200 than the battery 210. In some embodiments, the battery 210 could be embedded in the footwear in a position that does not permit access to the battery 210, which could be rechargeable, or non-replaceable.

Figure 3:
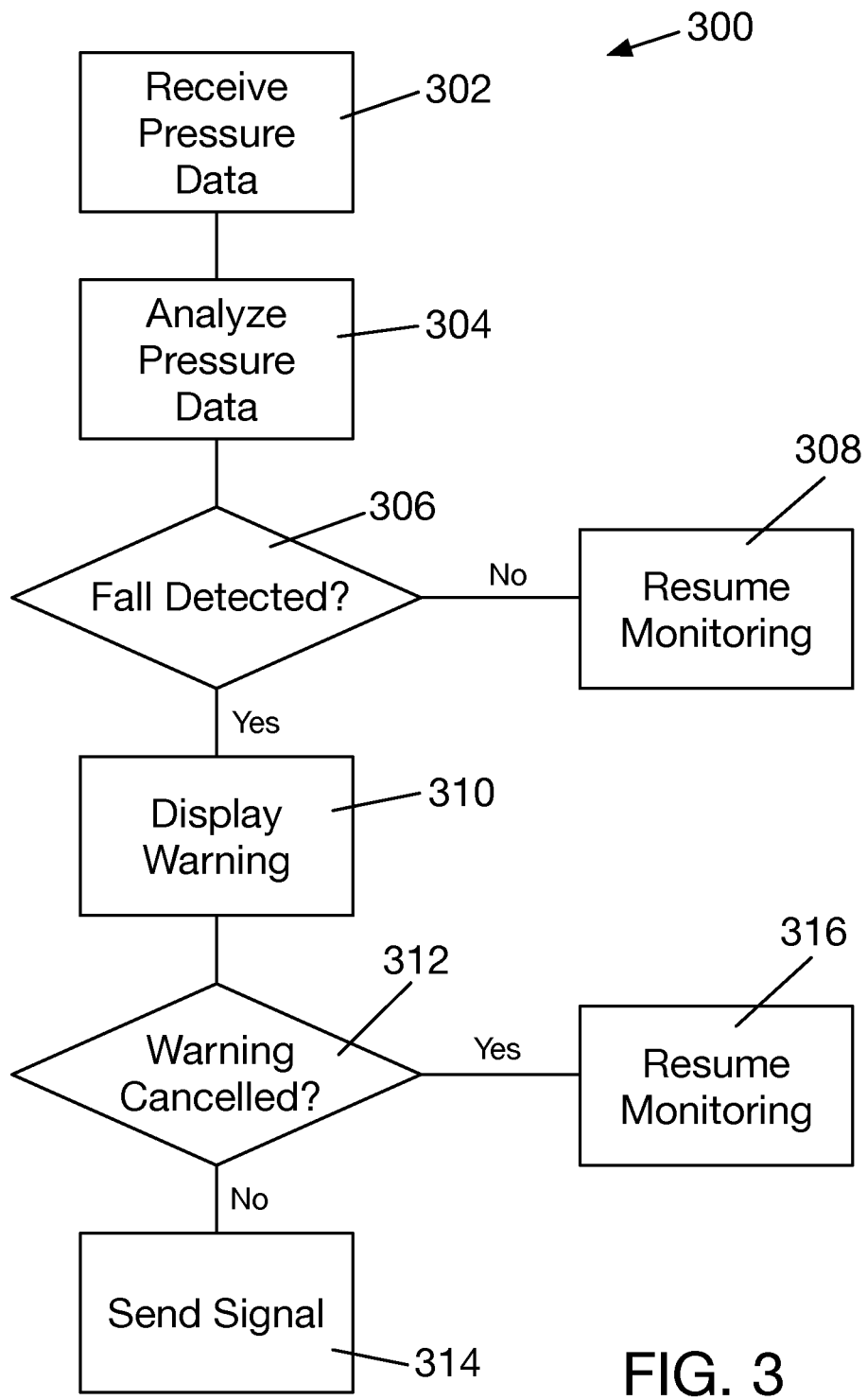
FIG. 3 is a flowchart of a method of detecting a fall in accordance with an embodiment of the disclosure.

FIG. 3 shows a method of detecting a fall using an embodiment of the fall detection system of the disclosure. The method 300 is employed with an embodiment of the footwear in which the left footwear and the right footwear transmit pressure information in substantially real-time, or in bursts at short intervals (generally ranging from about a few milliseconds to about a minute), to a mobile device, such as a smartphone, through a short-range communication protocol, such as the Bluetooth communication protocol. A processor executing an application installed in the memory of the mobile device processes the activities of the method 300.

At 302, the application receives foot step pressure and timing data from front and rear sensors from both footwear items. These data are stored in the mobile device until data for a predetermined length of time are received.

At 304, the data are analyzed, to determine if any fall, near-fall, or other abnormal incident has occurred. Sudden absence of pressure from both feet generally indicates a fall. It should be noted that, sometimes, when an elderly person falls, the pace and speed of the fall may be quite slow and gentle, yet the fall may still cause significant trauma. Thus, it may be desirable to look for more than just sudden absence of pressure from both feet. Other patterns, based on the time interval regularity of foot pressure, and irregularity between the front sensor and rear sensor on both left and right feet may also be used to detect abnormalities other than falls, including irregularities in gait, limping, or advance prediction of a fall. Additionally, if the user has only one foot, or is usually in a wheelchair, and only walking occasionally and with difficulty, walking patterns and behaviors may be substantially different from those found in other users. Accordingly, individualized patterns may be used to detect falls or other abnormalities. In some embodiments, an abnormality may be detected when there is a sudden deviation from the normal patterns associated with the individual user.

In some embodiments, the analysis of the data may be personalized, to take into account individual variations in pressure sensor patterns and to determine individual walking patterns and behavior. These personalized patterns and individual data can be stored, so that the personalized analysis can be adjusted over time, as more data are collected.

At 306, it is determined whether a fall has been detected. In some embodiments, the system will determine whether a fall or other abnormality has been detected to determine whether a warning or alarm should be raised. If no fall has been detected, monitoring will be continued at 308.

At 310, if a fall or other abnormality has been detected, an on-screen warning is displayed on the mobile device. This warning may, optionally, be accompanied by a sound, to alert the user to the warning. Once the warning is displayed, the user is given a predetermined period of time, generally between about 10 seconds and about two minutes, during which the warning may be canceled. In some embodiments a warning may also be triggered by other emergencies. For example, if the mobile device is also communicating with, e.g., a pacemaker, a warning or an immediate event signal could be triggered based on data received from the pacemaker. In some embodiments, the user may also manually trigger a warning or an immediate event signal, to indicate a need for assistance.

At 312, it is determined whether the warning has been canceled, and at 314, if the warning was not canceled (i.e., there has been no response to the warning from the user), then a fall detection signal or other event signal will be sent by the mobile device to one or more caregivers. If the mobile device has GPS or other location capability, then the fall detection or event signal may include the location of the user. In some embodiments, this location information will only be sent if it is determined that the user is away from home. Otherwise, the signal will simply indicate that the user is home. In some embodiments, other technologies, such as cell-based location systems, or location systems based on proximity to Wi-Fi receivers may be used to locate the mobile device if GPS is not available. Such systems could also be used to enhance the location information when GPS is available on the mobile device.

The caregiver may be emergency services, a medical provider, a designated family member or relative, a friend or network of friends, or another service or person who provides care for or is responsible for monitoring the user. The caregiver receiving the fall detection or event signal may be a predetermined caregiver, and may be designated by the user, or by someone other than the user, such as a medical provider. In some embodiments, the fall detection or event signal may be sent to multiple caregivers, or to different caregivers, depending on the event that triggered the signal, the time and/or date of the signal, and/or the location of the user.

If the warning was cancelled, then the mobile device will not further report the incident, and at 316, monitoring will resume. In some embodiments, following the cancellation of a warning, monitoring will resume only once regular foot pressure is detected.

Figure 4A:
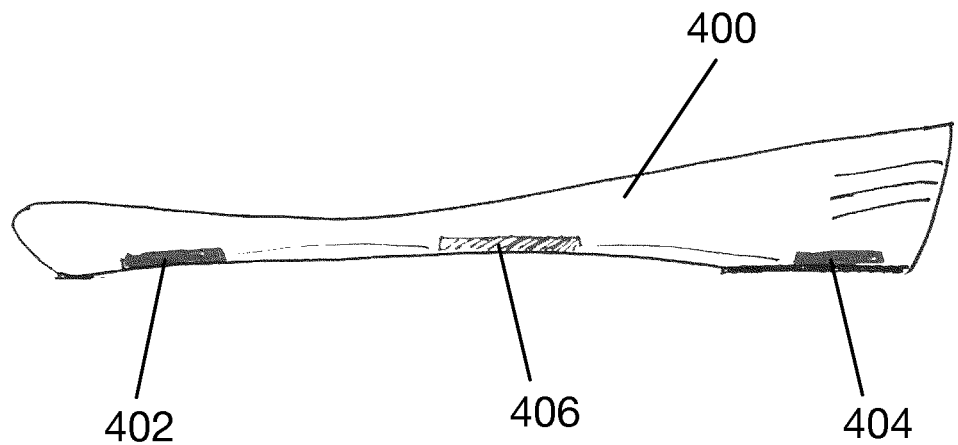
FIGS. 4A and 4B show fall-detection footwear in accordance with an embodiment of the disclosure.
Figure 4B:
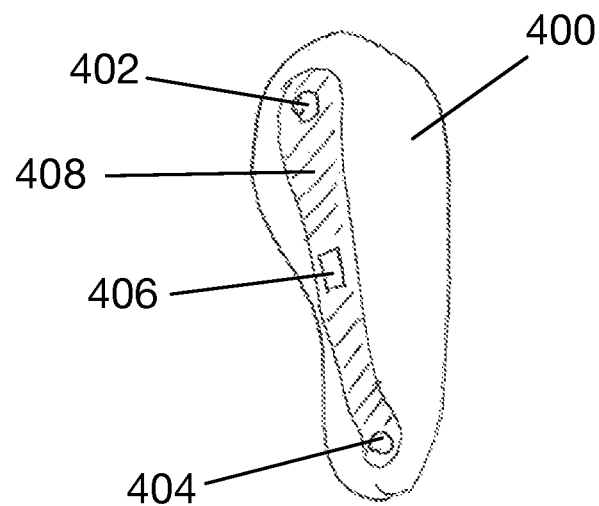

FIGS. 4A and 4B show components of another embodiment. Although the embodiment is described in terms of an insole, it will be understood that the same configuration could be used, mutatis mutandis, in any other footwear, such as shoes, socks, slippers, boots, and the like, or in prosthetic devices, such as prosthetic feet or legs, or in or attached to a cane, crutch, or other assistance device.

As shown in FIG. 4A, the footwear 400, which is shown for illustrative purposes as an insole, includes a front pressure sensor 402, a rear pressure sensor 404, and an electronics package 406. The front pressure sensor 402 and the rear pressure sensor 404 are electrically connected to the electronics package 406. As discussed above, the front pressure sensor 402 and rear pressure sensor 404 may be positioned so that they will be beneath the ball of the foot and the heel, respectively, though other positioning is also possible, as are additional pressure sensors, or sensors that detect pressure under substantially the entire foot. As above, the pressure sensors 402 and 404 may be any kind of pressure or force sensor, such as force-sensitive resistors or piezoelectric force sensors.

The electronics package 406 includes communications circuitry (not shown separately), which may be short-range communications circuitry (though long range or wide-area communications circuitry is also possible), such as Bluetooth circuitry, NFC circuitry, or circuitry supporting a body-area or personal-area network. The electronics package 406 may also include a controller (not shown separately), which may be a microcontroller, and may, in some embodiments, be integrated with the communications circuitry. The controller may control the gathering of data from the pressure sensors, control the transmission of data via the communication circuitry, and may perform other control functions in the footwear 400. The electronics package 406 also includes a power source (not shown separately), such as a battery, which may be a rechargeable battery. The electronics package 406 may also include an antenna (not shown), located within the footwear 400, and electrically connected to the communications circuitry.

Although the electronics package 406 is shown as being located in a central position within the footwear 400, other locations within the footwear 400 are also possible, without substantially affecting the operation of the electronics package 406 or of the footwear 400.

As shown in FIG. 4B, the sensors, including the front pressure sensor 402 and the rear pressure sensor 404, as well as the electronics package 406, may be enclosed within a flexible enclosure 408. The flexible enclosure 408 may be impermeable to liquids, since the footwear may be subjected to moist or wet conditions, due to sweat, water, and washing. In some embodiments, the flexible enclosure 408 and the electronics package 406 may be heat-resistant, to withstand machine washing at an elevated temperature. In some embodiments, the flexible enclosure may be a synthetic rubber compound that envelops the pressure sensors 402 and 404, as well as the electronics package 406 inside of the footwear 400. In some embodiments, the flexible enclosure 408 may be the footwear 400 itself, which may be a molded rubber product that encases the sensors 402 and 404, as well as the electronics package 406. In some embodiments, the entire footwear 400 may be washable in water.

The power source of the footwear 400 (as well as the footwear 200, described with reference to FIGS. 2A and 2B), may be a replaceable battery, a non-rechargeable battery, or a rechargeable battery, which is generally a part of the electronics package 406. This power source provides power for all of the electronic components of the footwear 400. It may be desirable for the power source to provide power for as long as possible, to reduce the frequency of battery replacement and/or recharging. One way to lengthen the time over which the power source provides sufficient power to the electronic components of the footwear 400 is for those electronic components to be low-power components. Another way of lengthening the time over which the power source provides sufficient power is to limit the time during which the electronic components operate. For example, instead of using the communications circuitry in the electronics package 406 to maintain a continuous connection (i.e., continuously using power) with a mobile device, the communications circuitry may send its data in bursts, shutting down the communications circuitry, or switching it to a low-power mode, such as a "sleep" mode, between bursts. Similarly, the controller in the electronics package 406 might operate in bursts, as it is needed, switching into a low-power or "sleep" mode between short bursts of activity. It will be understood that these ways of saving power may be applied in the footwear of FIGS. 2A and 2B, as well as in the footwear of FIGS. 4A and 4B, as well as in other embodiments of footwear in accordance with the present disclosure.

FIGS. 5-9 show various ways of recharging a power source that is included in footwear, such as the footwear 200 of FIGS. 2A and 2B, or the footwear 400 of FIGS. 4A and 4B. It will be understood that the recharging systems described below with reference to FIGS. 5-9 may be used in various embodiments of footwear in accordance with the present disclosure, for recharging a rechargeable battery or other rechargeable power source. It will further be understood that the recharging systems of FIGS. 5-8 may be used in combination with each other, so that two or more of them may be combined to provide power for recharging a rechargeable battery or other rechargeable power source.

Figure 5A:
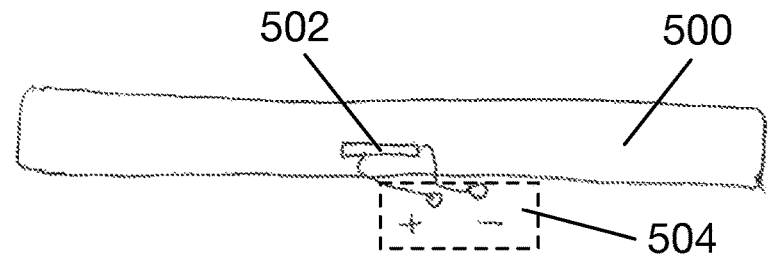
FIGS. 5A and 5B show fall-detection footwear having direct charging of a rechargeable power supply, in accordance with an embodiment of the disclosure.
Figure 5B:
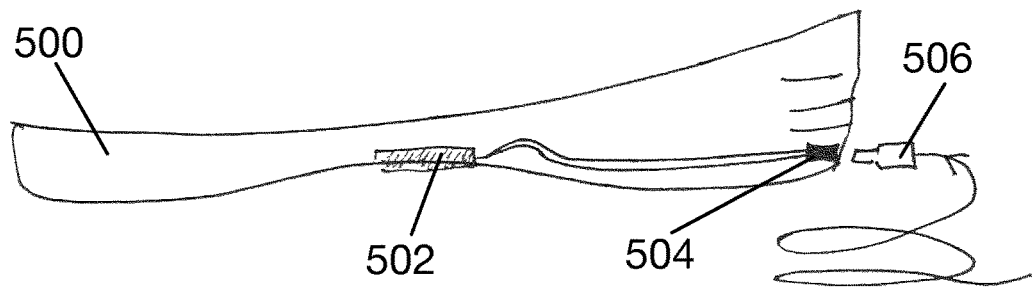

FIGS. 5A and 5B show a direct charge system for recharging a rechargeable power source in footwear in accordance with the disclosure. The footwear 500 includes a rechargeable power source 502, such as a rechargeable battery, that has an electrical connection 504 to an exterior, user accessible portion of the footwear 500. An external power supply (not shown) may be connected to the electrical connection 504 to recharge the rechargeable power source 502, using an external cable 506. The external cable 506 may be a conventional power cable, with any of a variety of connectors that may be connected to the electrical connection 504. For example, the external cable 506 may be a USB cable, for providing power to the footwear 500 via a powered USB source. In some embodiments, the power supply may provide direct current (DC). In some embodiments, the power supply may provide alternating current (AC).

Figure 6A:
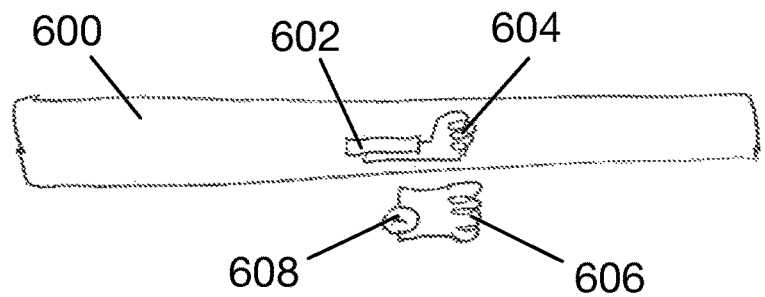
FIGS. 6A and 6B show fall-detection footwear having induction charging of a rechargeable power supply, and an induction charger, in accordance with an embodiment of the disclosure.
Figure 6B:
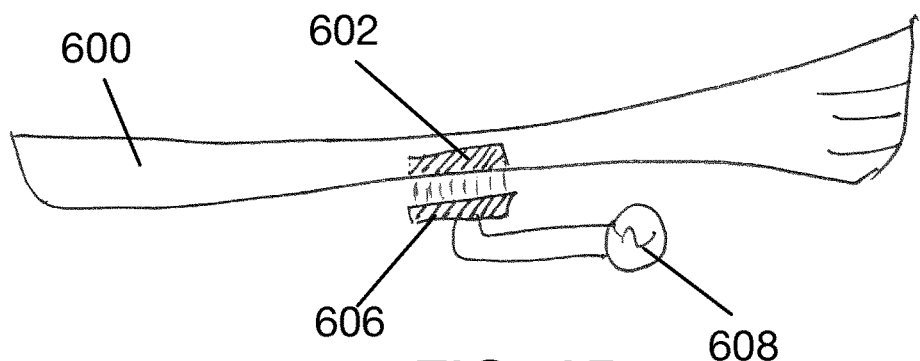

FIGS. 6A and 6B show an induction charger for recharging a rechargeable power source in footwear in accordance with the disclosure. The footwear 600 includes a rechargeable power source 602, such as a rechargeable battery, that is electrically connected to an internal induction coil 604, located within the footwear 600 and near an external surface of the footwear 600. An external induction coil 606, which may be powered by a more permanent power source 608 (which may be an AC power source), is inductively coupled to the internal induction coil 604 to supply power for recharging the rechargeable power source 602. In some embodiments, the external induction coil 606 may be embedded in an external charging stand, which may be adapted to accommodate the footwear 600 during charging.

Figure 7A:
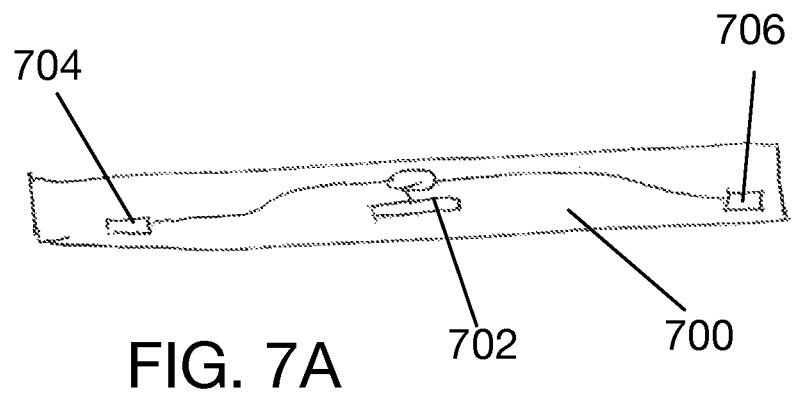
FIGS. 7A and 7B show fall-detection footwear having piezo-elements for charging a rechargeable power supply, in accordance with an embodiment of the disclosure.
Figure 7B:
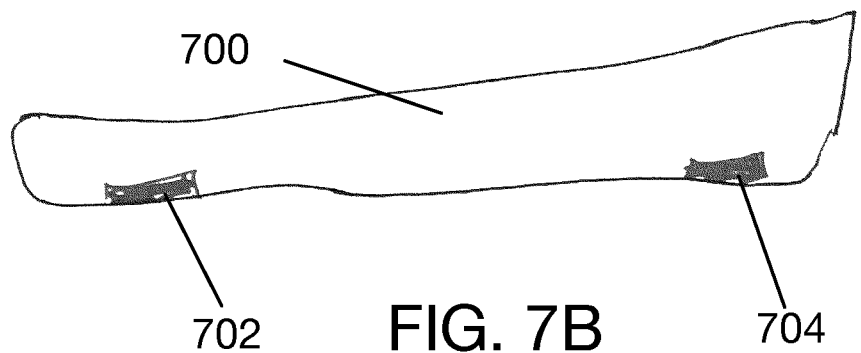

FIGS. 7A and 7B show a piezoelectric charger for recharging a rechargeable power source in footwear in accordance with the disclosure. The footwear 700 includes a rechargeable power source 702, such as a rechargeable battery, that is electrically connected to a front piezo element 704 and a rear piezo element 706. As pressure is applied and released on the front piezo element 704 and the rear piezo element 706, for example, during walking, power is generated by the piezo elements that can be used to recharge the rechargeable power source 702. Since piezo elements are also able to be used as pressure sensors, in some embodiments, the front piezo element 704 and the rear piezo element 706 may be the same as the front and rear pressure sensors that are used in various embodiments of fall-detection footwear in accordance with the disclosure. In some embodiments, more than two piezo elements may be used for generating power, as well as for sensing pressure.

Figure 8:
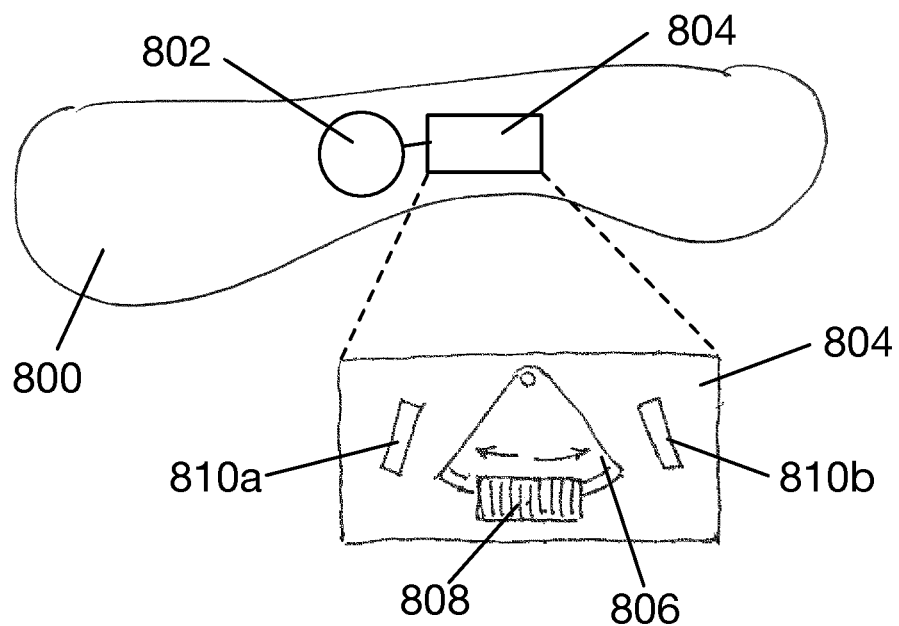
FIG. 8 shows fall-detection footwear having electromechanical charging of a rechargeable power supply, in accordance with embodiments of the disclosure.

FIG. 8 shows an electro-mechanical charger for recharging a rechargeable power source in footwear in accordance with the disclosure. The footwear 800 includes a rechargeable power source 802, such as a rechargeable battery, that is electrically connected to a kinetic generator 804, which generates power for recharging the rechargeable power source 802 from the user's movement.

In the embodiment illustrated in FIG. 8, the kinetic generator 804 includes a swing pendulum 806, a coil 808, and stops 810a and 810b. The swing pendulum 806 is magnetic, and motion from walking causes a magnetic portion of the swing pendulum 806 to sweep across the coil 808, generating current that can be used to recharge the rechargeable power source 802. The stops 810a and 810b limit the motion of the swing pendulum, but, in some embodiments, one or both of the stops 810a and 810b may be piezo elements, which may generate further power from the impact force of the swing pendulum 806 against the stops 810a and 810b. It will be understood that other designs for kinetic generators could also be employed to charge the rechargeable power source 802.

In the embodiment illustrated in FIG. 8, the kinetic generator 804 is oriented in a horizontal direction, to generate power from horizontal motion of the footwear 800. Such horizontal motion corresponds to the shuffling gait that is common in elderly people. Thus, the horizontal orientation of the kinetic generator 804 may generate more power when used by the elderly than, for example, an orientation of the kinetic generator that generates power from vertical motion of the user's foot. It will be understood that other orientations of the kinetic generator could be used.

Figure 9A:
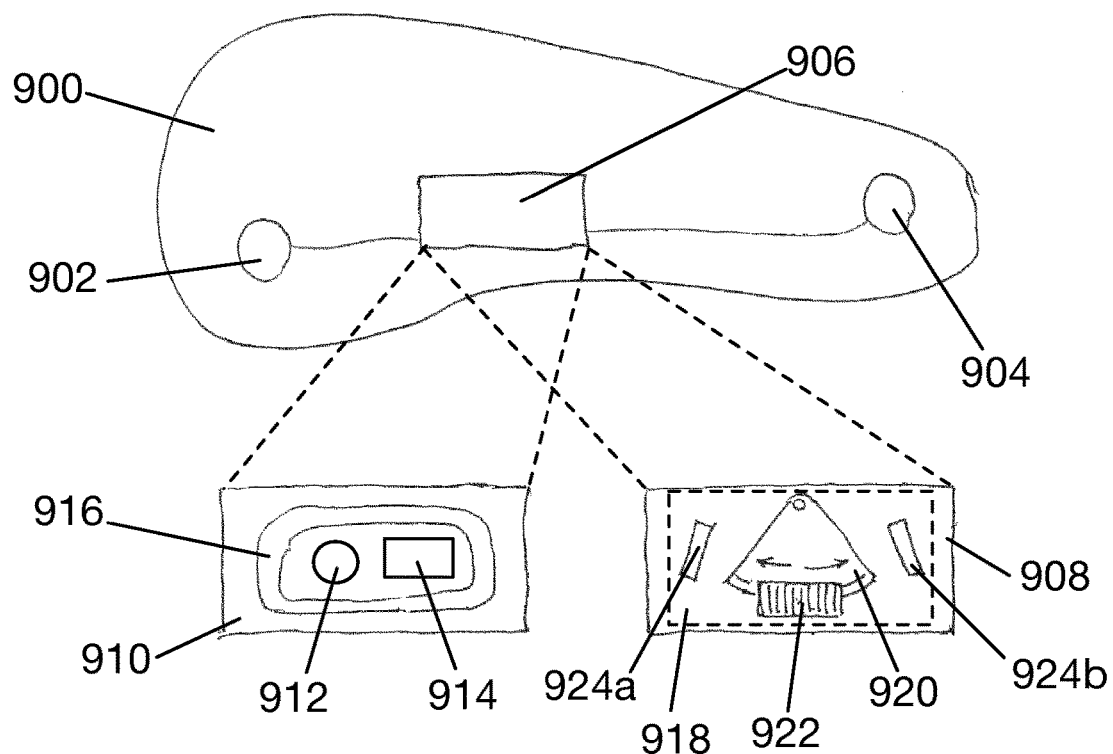
FIGS. 9A and 9B show fall-detection footwear with a combined recharging system, in accordance with an embodiment of the disclosure.
Figure 9B:
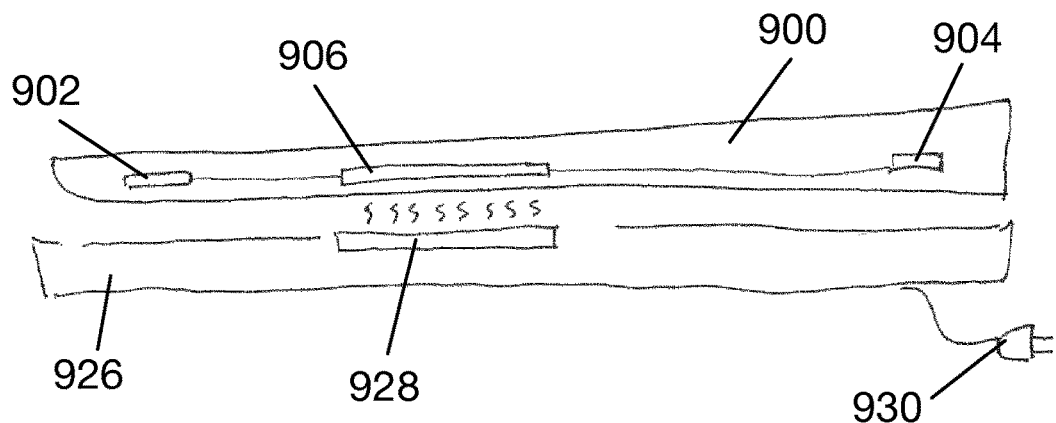

FIGS. 9A and 9B show an embodiment of fall-detection footwear, in which multiple recharging systems are combined to provide power to recharge a rechargeable power source. While footwear 900 is shown as having induction charging, piezoelectric charging, and electro-mechanical charging, as illustrated above in FIGS. 6, 7, and 8, respectively, it will be understood that other combinations of charging systems could be used.

The footwear 900 is shown for illustrative purposes as an insole, but could be a shoe, sock, slipper, boot, or other footwear, or could be built into, attached to, or worn on prosthetic devices, such as prosthetic feet or legs, or built into or attached to a cane, crutch, or other assistance device. The footwear 900 includes a front pressure sensor 902, a rear pressure sensor 904, and an electronics package 906. The electronics package 906 includes two layers: a top layer 908; and a bottom layer 910.

The bottom layer 910 includes a rechargeable power source 912, such as a rechargeable battery, a controller 914, which may include communications circuitry (not shown separately), and an internal induction coil 916, to receive energy induced by an external induction coil for recharging the rechargeable power source 912. In some embodiments, the communication circuitry (not shown separately) may be separate from the controller. An antenna (not shown), embedded within the footwear 900, may be electrically connected to the communication circuitry.

The top layer 908 includes a kinetic generator 918, such as is described above, with reference to FIGS. 8A and 8B.

For illustrative purposes, the kinetic generator 918 includes a swing pendulum 920, a coil 922, and stops 924a and 924b. The swing pendulum 920 is magnetic, and motion from walking causes a magnetic portion of the swing pendulum 920 to sweep across the coil 922, generating current that can be used to recharge the rechargeable power source 912. The stops 924a and 924b may be piezo elements, which may generate further power from the impact force of the swing pendulum 920 against the stops 924a and 924b. It will be understood that other designs for kinetic generators could also be employed.

The front pressure sensor 902 and the rear pressure sensor 904 are electrically connected to the electronics package 906. The front pressure sensor 902 and rear pressure sensor 904 may be positioned so that they will be beneath the ball of the foot and the heel, respectively, though other positioning is also possible, as are additional pressure sensors. The pressure sensors 902 and 904 may also include a piezo element that generates power for recharging the rechargeable power source 912. In some embodiments, the pressure sensors 902 and 904 are piezoelectric force sensors that both detect pressure and generate power for recharging the rechargeable power source 912. In some embodiments, the pressure sensors 902 and 904 may be force-sensitive resistors or other force or pressure sensors, combined with or coupled to piezo elements for recharging the rechargeable power source 912.

Although the electronics package 906 is shown as being located in a central position within the footwear 900, other locations within the footwear 900 are also possible, without substantially affecting the operation of the electronics package 906 or of the footwear 900.

As shown in FIG. 9B, when it is not in use, the footwear 900 may be placed on a footwear rest 926, which may be adapted to accommodate the footwear 900, and is connected to a more permanent power source, for example, through power cord 930. The footwear rest 926 includes an induction coil 928, which may be inductively coupled to the internal induction coil 916 for recharging the rechargeable power source 912, when the footwear 900 is placed on the footwear rest 926.

While the invention has been shown and described with reference to specific embodiments, it should be understood that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A fall detection system comprising:
a right footwear item and a left footwear item, each of the right and left footwear items including:
at least two foot pressure sensors;
communications circuitry configured to transmit foot pressure signals from the at least two pressure sensors to a mobile device;
a rechargeable power source connected to the communications circuitry, the rechargeable power source providing power to the communications circuitry; and
a kinetic generator that generates power for recharging the rechargeable power source; and
a mobile device executing an application that causes the mobile device to:
receive transmitted foot pressure signals from the communications circuitry of the footwear;
analyze the foot pressure signals to determine whether a wearer of the footwear items has fallen;
display a warning if it is determined that the wearer of the footwear items has fallen, along with an option to cancel the warning; and
send a signal to a caregiver if the warning has not been canceled within a predetermined period of time.

2. The fall detection system of claim 1, wherein the application causes the mobile device to analyze the foot pressure signals by determining that the wearer of the footwear items has fallen if the foot pressure signals from both the right footwear item and the left footwear item indicate a drop to zero or nearly zero pressure.

3. The fall detection system of claim 1, wherein the application further causes the mobile device to determine and store a normal foot pressure pattern for the wearer of the footwear items, based on the foot pressure signals received from the footwear items.

4. The fall detection system of claim 3, wherein the application further causes the mobile device to display a warning if there is a sudden deviation from the normal foot pressure pattern for the wearer of the footwear items, along with an option to cancel the warning.

5. The fall detection system of claim 1, wherein the at least two foot pressure sensors comprise a front foot pressure sensor, configured to be located approximately beneath a ball of the wearer's foot, and a rear foot pressure sensor, configured to be located approximately beneath a heel of the wearer's foot.

6. The fall detection system of claim 1, wherein the right footwear item and the left footwear item comprise insoles.

7. The fall detection system of claim 1, wherein the right footwear item and the left footwear item comprise a shoe, a sock, a slipper, or a boot.

8. The fall detection system of claim 1, wherein at least one of the right footwear item and the left footwear item is built into or attached to a prosthetic device or walking assistance device.

9. The fall detection system of claim 1, wherein the at least two pressure sensors, the communication circuitry, and the rechargeable power source are contained within a flexible enclosure that is impervious to liquids.

10. The fall detection system of claim 1, wherein each of the right footwear item and the left footwear item further comprises an induction charger for recharging the rechargeable power source.

11. The fall detection system of claim 1, wherein each of the right footwear item and the left footwear item further comprises a plurality of piezo elements that generate power for recharging the rechargeable power source.

12. The fall detection system of claim 1, wherein the at least two foot pressure sensors comprise piezo elements that sense foot pressure and that generate power for recharging the rechargeable power source.

13. The fall detection system of claim 1, wherein the kinetic generator comprises a swing pendulum having a magnetic portion, and a coil, the swing pendulum configured such that when the wearer of the footwear is walking, the magnetic portion of the swing pendulum sweeps across the coil to generate power.

14. The fall detection system of claim 13, wherein the kinetic generator further comprises two stops disposed so that the swing pendulum strikes one of the stops at each end of its swinging motion, and wherein at least one of the stops comprises a piezo element that generates power for recharging the rechargeable power source.

15. The fall detection system of claim 1, wherein the mobile device comprises a smartphone.

\* \* \* \* \*